United States Patent
Gottlieb

(10) Patent No.: US 9,476,810 B2
(45) Date of Patent: Oct. 25, 2016

(54) AUTOMATED SAMPLE PREPARATION

(75) Inventor: Paul Gottlieb, West End (AU)

(73) Assignee: FEI COMPANY, Hillsboro, OR (US)

( * ) Notice: Subject to any disclaimer, the term of this patent is extended or adjusted under 35 U.S.C. 154(b) by 273 days.

(21) Appl. No.: 14/110,576

(22) PCT Filed: Apr. 23, 2012

(86) PCT No.: PCT/US2012/034682
§ 371 (c)(1),
(2), (4) Date: Oct. 8, 2013

(87) PCT Pub. No.: WO2012/145751
PCT Pub. Date: Oct. 26, 2012

(65) Prior Publication Data
US 2014/0048972 A1     Feb. 20, 2014

Related U.S. Application Data

(60) Provisional application No. 61/478,351, filed on Apr. 22, 2011.

(51) Int. Cl.
  *G01N 1/28*     (2006.01)
  *G01N 1/06*     (2006.01)
  *G01N 1/36*     (2006.01)

(52) U.S. Cl.
  CPC  *G01N 1/28* (2013.01); *G01N 1/06* (2013.01); *G01N 1/286* (2013.01); *G01N 1/36* (2013.01); *H01J 2237/201* (2013.01); *H01J 2237/2007* (2013.01)

(58) Field of Classification Search
  CPC .... G01N 1/06; G01N 1/28; G01N 2001/063; B29C 67/248; E21B 49/00
  USPC ............... 264/129; 425/94, 173, 308
  See application file for complete search history.

(56) References Cited

U.S. PATENT DOCUMENTS

| 4,435,507 A | 3/1984 | Stenkvist |
| 4,834,943 A * | 5/1989 | Yoshiyama ............... G01N 1/36 118/429 |

(Continued)

FOREIGN PATENT DOCUMENTS

| DE | 19743590 A1 * | 5/1999 | ............... G01N 1/06 |
| EP | 2199778 A1 | 6/2010 | |

(Continued)

OTHER PUBLICATIONS translation of DE19743590.*

(Continued)

*Primary Examiner* — Alison L Hindenlang
*Assistant Examiner* — Mohamed K Ahmed Ali
(74) *Attorney, Agent, or Firm* — Scheinberg & Associates, P.C.; Michael O. Scheinberg

(57) ABSTRACT

Mineral samples for use in analytical instruments are created by a system that greatly reduces the sample preparation time and facilitates automation. For example, in some implementations, rather than grinding to expose the interior of mineral particles in sample plug containing mineral particles in an epoxy compound, the sample plug is sliced with a saw, which more rapidly provides in many applications a sufficiently smooth surface on the exposed particle surfaces for observation. Rather than slowly mixing a slow curing epoxy to avoid introducing bubbles into the sample plug, some implementations use a fast settle fixative and a mechanical mixture that avoid bubbles.

13 Claims, 9 Drawing Sheets

(56) References Cited

U.S. PATENT DOCUMENTS

| | | | |
|---|---|---|---|
| 6,140,643 | A | 10/2000 | Brown et al. |
| 6,393,906 | B1 | 5/2002 | Vityk et al. |
| 7,490,009 | B2 | 2/2009 | Gottlieb et al. |
| 7,979,217 | B2 | 7/2011 | Gottlieb et al. |
| 2001/0053820 | A1* | 12/2001 | Yeager .................. C08G 65/485 525/186 |
| 2008/0115640 | A1* | 5/2008 | Ranner ................ B23D 45/003 83/98 |
| 2008/0197526 | A1* | 8/2008 | Shafi ....................... B29C 70/48 264/137 |
| 2010/0243901 | A1* | 9/2010 | Okamoto .............. B29C 43/003 250/339.07 |
| 2011/0301869 | A1 | 12/2011 | Gottlieb et al. |

FOREIGN PATENT DOCUMENTS

| | | |
|---|---|---|
| KR | 20-2000-0012548 | 7/2000 |
| WO | 8200200 | 1/1982 |
| WO | 8701803 | 3/1987 |

OTHER PUBLICATIONS

Ashton, Edward A., "Multialgorithm solution for automated multispectral target detection," Society of Photo-Optical Instrumentation Engineers, 1999, pp. 717-724, vol. 38, No. 8.

Benz, Ursula, C. et al., "Multi-resolution, object-oriented fuzzy analysis of remote sensing data for GIS-ready information," Journal of Photogrammetry & Remote Sensing, 2004, pp. 239-258, vol. 58.

Fandrich, Rolf, et al., "Modern SEM-based mineral liberation anaylsis," International Journal of Mineral Processing, 2007, pp. 310-320, vol. 84.

Ghassemian, Hassan, et al., "Object-Oriented Feature Extraction Method for Image Data Compaction," IEEE Control Systems Magazine, 1988, pp. 42-48.

Hazel, Geoffrey G., "Object-level processing of spectral imagery for detection of targets and changes using spatial-spectral-temporal techniques," Proceedings of SPIE, 2001, pp. 380-390, vol. 4381.

Jana, Dipayan, "Sample Preparation Techniques for Petrographic Examinations of Construction Materials: A State-of-the-Art Review," Proceedings of the Twenty-Eighth Conference on Cement Microscopy, 2006, pp. 23-70.

Newbury, Dale, E., "Chemical compositional mapping by microbeam analysis at the micrometer scale and finer," Microelectronics Journal, 1997, pp. 489-508, vol. 28.

Pirrie, Duncan, et al. "Rapid quantitative mineral and phase analysis using automated scanning electron microscopy (QemSCAN); potential applications in forensic geoscience," Forensic Geoscience: Principles, Techniquest and Applications, Geological Society, 2004, pp. 123-136, vol. 232.

\* cited by examiner

AUTOMATED SAMPLE PREPARATION

TECHNICAL FIELD OF THE INVENTION

The invention relates to preparing sample for analysis and in particular to provide multiple novel ways to reduce the time required for preparing samples and to facilitate automation of sample preparation.

BACKGROUND OF THE INVENTION

Automated Mineralogy (AM) systems, such as the QEM-SCAN and MLA from FEI Company, have been used for many years to determine minerals present in mines in order to determine the presence and distribution of valuable minerals. Such systems direct an electron beam toward the sample and measure the energy of x-rays coming from the material in response to the electron beam. One such process is called "energy dispersive x-ray analysis" or "EDS," which can be used for elemental analysis or chemical characterization of a sample.

In EDS analysis, a high-energy beam of charged particles such as electrons or protons, or a beam of x-rays, is focused into the sample being studied to stimulate the emission of x-rays from the sample. The energy of the x-rays emitted from a specimen is characteristic of the atomic structure of the elements making up the specimen. By measuring the number and energy of the x-rays emitted from a specimen using an energy-dispersive spectrometer, and comparing the measured spectra to a library of reference spectra of known compositions, the unknown elemental composition of the specimen can be determined. EDS analysis, especially when coupled with back-scattered electron (BSE) analysis, can also be used to quantify a wide range of mineral characteristics, such as mineral abundance, grain size, and liberation. Mineral texture and degree of liberation are fundamental properties of ore and drive its economic treatment, making this type of data invaluable to geologists, mineralogists and metallurgists who engage in process optimization, mine feasibility studies, and ore characterization analyses.

Mineral analysis systems of this type are also used in the oil and gas industry, as well as in mining. Drill cuttings (drill bit-induced rock chips) and diamond drill cores can be analyzed to allow geologists to determine the exact nature of the material encountered during drilling, which in turn allows more accurate predictions as to the material still ahead of the drill, thus reducing risk in exploration and production. During drilling, a liquid referred to as "mud" is injected into the well to lubricate the drill and return the cuttings out of the well. A sample can be taken from the mud that includes cuttings from the drill. Great importance is often placed on documenting cuttings and cores as accurately as possible, both at the time of drilling and post-drilling. Characterizing down-hole lithological variation in a reservoir sequence is a critical requirement in exploration and production wells, and mineralogical and petrographic studies underpin the fundamental understanding of reservoir and seal characteristics. Traditional optical microscopes, scanning electron microscopes (SEM), electron probe microanalyzer (EPMA) and x-ray diffraction (XRD) analysis methods are well established and widely used within the industry.

A problem inherent in Automated Mineralogy is how to obtain representative, useful, accurate, and precise three-dimensional microscopic quantitative knowledge about a huge three dimensional macroscopic population by means of tiny two dimensional microscopic samples. One of the most important considerations for this type of analysis is whether the prepared sample being analyzed is truly a representative sample. For this reason, sample preparation techniques are particularly important for meaningful analysis. Samples suitable for use in analytical instruments such as QEM-SCAN and MLA systems should be prepared so that the material to be analyzed can be presented to the instrument as a flat, carbon coated surface. Typically, material to be analyzed, such as material retrieved from a mine, is carefully sampled from the mine, crushed, and mixed with epoxy in a mold. The sample mold is cured and then the sample is removed. The sample is ground to expose the interior of some of the particles, and then polished to produce a smooth surface. The surface is coated with a carbon film to form a conductive coating to prevent electrical charging by the electron beam, and the sample is typically observed using a camera to ensure that it was properly prepared before it is inserted into the vacuum chamber of the electron beam system.

To ensure that the results of the analysis are representative, the particles have to be uniformly distributed in the epoxy, so that when the sample is ground, the probability of exposing all particles is uniform. Using prior art methods of sample preparation, the process of preparing a suitable representative sample typically takes about 8 hours. This has long been considered acceptable in the mining industry. In the drilling industry, it would be desirable to obtain much faster feedback regarding the composition of the drill cutting in order to adjust the drilling process sooner.

Accordingly, what is needed is a method and apparatus for preparing suitable representative samples for EDS analysis, or other similar types of analysis, that allows the samples to be produced much more rapidly, preferably in less than one hour as opposed to the eight hour time frame of the prior art.

SUMMARY OF THE INVENTION

An object of the invention is to provide a system for quickly and repeatedly preparing a sample for EDS or other types of analysis.

In accordance with a preferred embodiment of the invention, a sample is prepared for analysis in a system, such as an electron beam system. In some embodiments, a sample composed of multiple particles is mixed with a fast setting fixing compound in a mold. The mold and particles are mixed using an automated mixer such as a planetary mixer while the fixing compound is curing to stabilize the position of the particles in the mold. Rather than removing a cured sample from the mold, the mold is sliced along with the sample to produce an observation surface that exposes the interior of sample particles. In some embodiments, the sliced surface is not subjected to any grinding or polishing process before observation. In some embodiments, a light polishing process may be applied before observation. A conductive coating is optionally applied over the surface before observation to prevent charging by the beam used in the analysis. Multiple slices may be made to increase the number of particles exposed for measurement from a single mold.

The foregoing has outlined rather broadly the features and technical advantages of the present invention in order that the detailed description of the invention that follows may be better understood. Additional features and advantages of the invention will be described hereinafter. It should be appreciated by those skilled in the art that the conception and specific embodiments disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a more thorough understanding of the present invention, and advantages thereof, reference is now made to the following descriptions taken in conjunction with the accompanying drawings.

The accompanying drawings are not intended to be drawn to scale. In the drawings, each identical or nearly identical component that is illustrated in various figures is represented by a like numeral. For purposes of clarity, not every component may be labeled in every drawing.

DETAILED DESCRIPTION OF PREFERRED EMBODIMENTS

Figure 1:
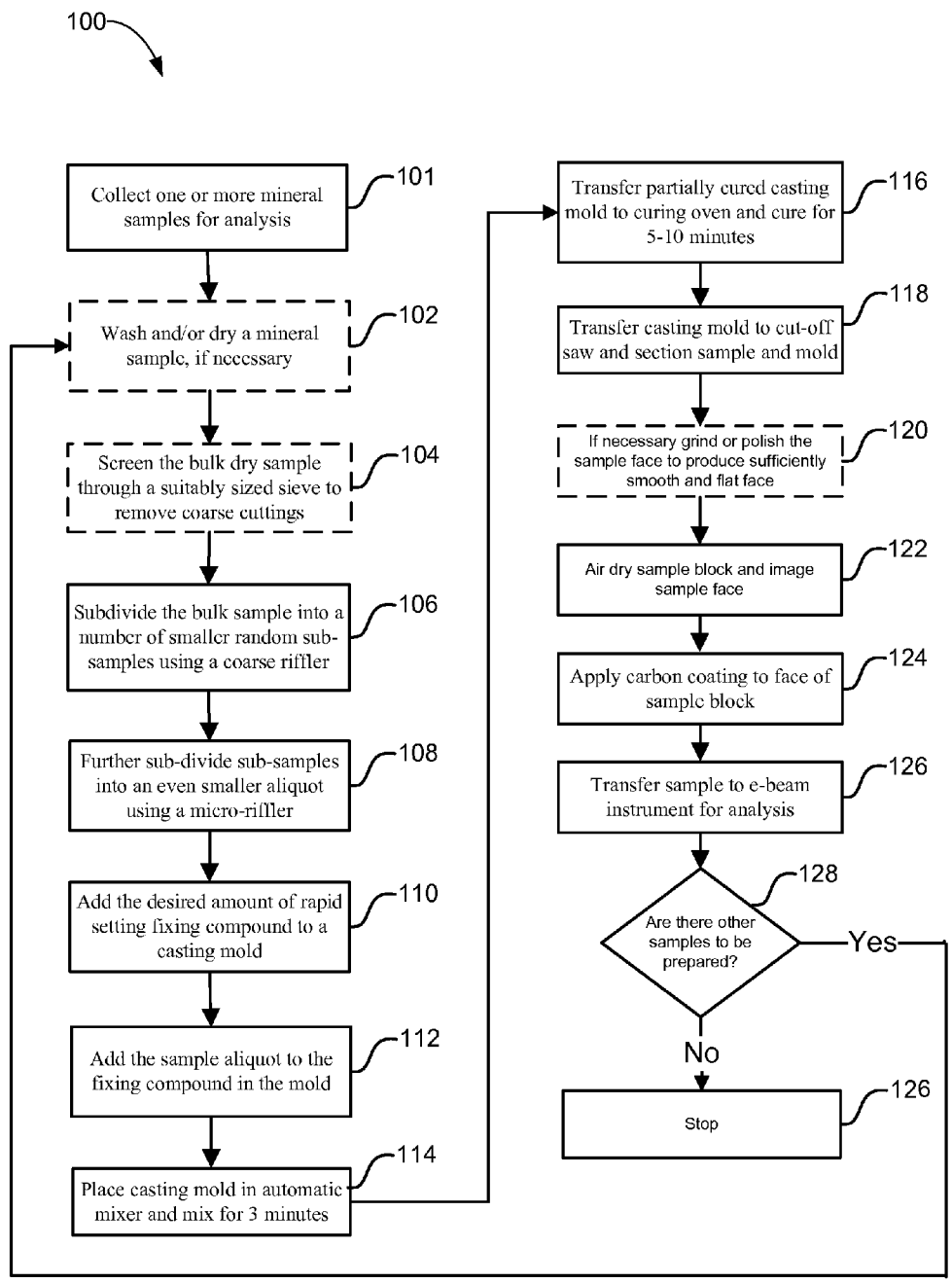
FIG. 1 is a flowchart of steps of a method of sample preparation according to preferred embodiments of the present invention.

A preferred method and apparatus according to the present invention produces representative samples from particulate materials from, for example, drilling cores or bulk material from a mine, that are suitable for an analysis such as an energy dispersive x-ray analysis (EDS). Further, sample preparation according to embodiments of the present invention can be completed significantly faster than the sample preparation methods of the prior art, typically in less than an hour instead of the 8 hours required when using the methods of the prior art. Preferred embodiments of the present invention generally include the creation of a representative sample from the bulk lot, casting of the block by the machine mixing of the sample with a rapid-setting epoxy resin, optionally curing in an oven, creating a random section by sawing through the block to produce a suitably flat sample face, often without the necessity of grinding or polishing, and finally coating the sample with a conductive layer of carbon.

Sample preparation preferably produces a representative mix of particles in a representative sample slice having a smooth flat surface. Producing a homogeneous mixture of particles and mounting medium is very desirable, and there are a number of important factors that determine the suitability of such a mixture, including the creation of a uniform mixture, the prevention of agglomeration, the random orientation of the particles, and the removal of bubbles. These factors were not always achieved by the prior art.

According to prior art methods of sample preparation, the sample particulate was mixed with a slow-setting epoxy and often with an "inert" low atomic number filler such as casein or graphite to prevent density segregation, to keep the individual particles from touching each other, and to maintain random orientation of the particles. In many prior art implementations, the density segregation was very marked and a rough "vertical section" was cut in the direction of the segregation to ensure random selection of particles. The vertical sections were then remounted horizontally in slow-setting epoxy, and the vertically cut surface was ground and polished, thus adding to the overall preparation time.

Using electron microscopy, including EDS and BSE analysis, a flat surface is desirable for these types of mineral analysis because it avoids unwanted artifacts such as shadowing that can affect the accuracy of the analysis. Also, stereology, or determining the three dimensional structure of the sample particles from 2D images, is much more accurate when a flat surface is imaged.

According to prior art methods of sample preparation, the sample particulate was mixed with slow-setting epoxy. It was thought that sample mixing while the epoxy was setting was necessary to produce an even distribution of the particulate sample. Using slow-setting epoxy, particularly for large particles results in density segregation whereby the heavier and larger particles sink to the bottom and are over-represented at the bottom of the mold. Using a rapid setting epoxy would require a more vigorous mixing because the epoxy would begin to harden so quickly. Vigorous mixing, however, was thought to introduce air bubbles into the epoxy mixture (frothing). Because a goal of sample preparation is to produce a flat sample face having a uniform and representative distribution of the particulate material, any bubbles present in the area of the sample casting block where the sample is sliced would affect the accuracy of the sample analysis. It was also extremely difficult to get an even distribution of the sample material in the epoxy before a faster setting epoxy hardened too much. As a result, prior art methods used a relatively slow setting epoxy (setting time of ~2 hrs) along with a slow stirring, typically by hand, to prevent particles from settling. According to the prior art, two further stages of preparation using heat and pressure or vacuum were used to remove bubbles from the mixture before the epoxy sets. Applicants believe that it was during this bubble removal time, while the epoxy must remain liquid, that the density segregation occurs. Prior art methods also required additional manual steps such as rolling and ultrasonic agitation to de-agglomerate very fine particles. Significantly, samples of particulate material have been prepared for EDS analysis using this combination of slow setting epoxy and slow hand stirring since the introduction of this type of EDS sample analysis in the late 1970s.

Once the cast sample was cured, according to prior art sample preparation methods, the sample was subjected to a number of grinding then polishing steps to create the section and to ensure that the sample face was perfectly flat. According to a typical prior art preparation method, the sample face would first be subjected to a grinding step, using for example 75 μm grit abrasive, and then possibly a second grinding step using a finer grit, for example 20 μm grit. After that, the sample would be polished using even finer abrasive material such as diamond paste and polishing pads, for example 6 μm abrasive polishing, followed by 3 μm polishing, followed by 1 μm polishing. The grinding and polishing steps alone typically took as much as 1 hour. Finally, to increase the size of the cast block and to hold a label, a further "back-fill" of slow-setting epoxy was used. The additional curing time for the back-fill added significantly to the overall curing time using prior art sample preparation methods.

As discussed above, a typical sample preparation using the prior art methods took around 8 hours. Because a large number of samples per site will typically need to be prepared and analyzed, the process usually involved teams of up to ten technicians continuously preparing samples. This type of process has been used to prepare mineral analysis samples for electron microscope and EDS analysis for decades with no significant improvement in the sample preparation process. In one implementation, some of the mixing steps of the prior art process have been automated to improve speed or efficiency. While the prior art sample preparation processes were adequate for many types of sample analysis, such as the analysis of samples from mining operations, in other areas, such as the analysis of drill cuttings, much faster feedback is needed to enable rapid decisions to be made based on the results of a few measurements. Applicants have discovered that some of the original assumptions regarding sample preparation may not be true. Further, proceeding contrary to accepted wisdom, Applicants have discovered that acceptable results can be obtained by eliminating or combining some of the steps previously thought to be essential.

For example, it was thought that using a relatively slow setting epoxy was necessary to produce an even distribution of the particulate sample, because vigorous mixing (which would be required with a rapid setting epoxy) introduced air bubbles into the epoxy mixture. Applicants discovered, however, that the frothing problem was not the result of the vigorous stirring itself, but rather appears to have been caused by combination of the consistency of the slower setting epoxy (which remains in a relatively liquid form for much longer than more rapid setting epoxy) and that the samples were stirred by hand. It appears that the typical hand stirring motion itself introduced the air bubbles, which must be removed while the epoxy is still liquid. In preferred embodiments of the present invention, Applicants use a much more rapid setting epoxy, one that rubberizes or hardens in less than 15 minutes, more preferably in less than 10 minutes, even more preferably in less than five minutes and most preferably in as little as three minutes. Further, instead of using hand stirring, Applicants use a mixing machine such as a planetary mixer to rapidly mix the epoxy and sample material, at a rotation speed of preferably greater than 500 rpm, more preferably greater than 1000 rpm, and most preferably approximately 2000 rpm. Using a fast setting epoxy with automatic mixing according to embodiments of the present invention shortens the stirring and epoxy setting time from approximately an hour down to 3-4 minutes whilst essentially eliminating bubbles and agglomeration. The use of rapid mixing also contributes to the de-agglomeration of fine particles, bubble removal, and particle segregation, all of which were addressed by separate time-consuming steps such as rolling and ultrasonic agitation according to the prior art.

Applicants have also discovered that, contrary to prior art practice, the sample surface after slicing is sufficiently smooth in many cases for viewing, making the grinding and polishing steps unnecessary. The elimination of the grinding/polishing steps is significant because these steps typically occupied a significant part of the sample preparation time using prior art methods.

For accurate and precise quantification of the mineral composition at a single analysis point, a very flat surface is required to prevent fluorescence and absorption. For this reason, samples prepared according to prior art methods were subjected to the multiple grinding and polishing steps described above to ensure that the sample face was perfectly flat. It appears, however, that the grinding and polishing steps themselves were causing additional surface damage and bias, thus requiring more and more polishing steps to create a flat surface. The surface finish after grinding is very poor, and the polishing stages were necessary to remove scratches created by the grinding process. Grinding and polishing are also done on a horizontal surface in prior art sample preparation, and cuttings removed by the process cause scratches in the surface which are removed by up to three stages of finer and finer polishing. Another bias introduced by grinding and polishing is the so-called "Holmes Effect" whereby polishing relief is created by the differential polishing of hard and soft material—in particular the minerals and epoxy mounting medium, but also between hard and soft minerals in the sample.

By eliminating the grinding and polishing steps altogether, Applicants have discovered that the sawed sample can be flat enough for many types of analysis. For applications such as the analysis of drill cuttings, quantitative results (which are typically thought to require an absolutely flat surface) are not as important as accurate mineral identification. Further, most modern analysis systems make use of multiple detectors of each type and combine the spectra in order to maximize the signal collected per electron (which speeds up processing time). Applicants have also discovered that the use of multiple detectors greatly decreases the likelihood of surface roughness resulting in shadowing, which would affect the accuracy of the analysis. Even for applications such as those in the mining industry when mineral quantification is more important, Applicants have discovered that by preparing the samples using a relatively fine fluid-cooled saw blade and sawing the sample vertically (so that the fluid can wash off the cuttings from the saw before they damage the exposed surface) the sample can be sectioned with little enough damage that typically no additional polishing is required. Several novel aspects of a preferred embodiment also facilitate the automation of the process, which, to Applicants' knowledge, has not been successfully automated before now. While some embodiments of the present invention are fully automated, other embodiments may automate less than all the steps, or even include all manual steps. Various improvements to the prior art process facilitate automation, but such improvements are also desirable for use in manual processes. Specifically, embodiments of the present invention lend themselves to automation because of the overall simplification of the process, including the removal of a number of prior art preparation steps altogether (as described herein). The use of the integral mold with separately labeled primary and secondary sections, as described above, also facilitates the automation process. Not only is the difficult-to-automate sample removal step eliminated, but the labeling of the primary and secondary sections makes it easier to track specific samples since the sample stays attached to the integral mold through the rest of the sample preparation process. Elimination of the grinding and polishing steps not only simplifies the process, it also eliminates a number of steps such as finish inspection during polishing and changing grinding/polishing pads that typically require human intervention.

A problem can arise when water-based cutting fluids are used on samples containing soluble minerals, such as halite, which are dissolved, and swelling-clay supported minerals which are preferentially removed from the sample surface during section creation. The effect occurs during both conventional grinding & polishing as well as during sawing because of the water-based cooling and lubrication fluid. A preferred method for this type of sample is to use an alternative cutting fluid such as kerosene, diesel fuel, and vegetable oils, such as canola oil, which do not create the problem.

A preferred method or apparatus of the present invention has many novel aspects, and because the invention can be embodied in different methods or apparatuses for different purposes, not every aspect need be present in every embodiment. Some of the steps such as curing in an oven and a final surface polish may be optionally included or deleted. In most cases, the epoxy cures sufficiently fast at room temperature. Moreover, many of the aspects of the described embodiments may be separately patentable.

FIG. 1 is a flowchart 100 of steps of a preferred method of the invention. The method of FIG. 1 can preferably be carried out by way of an automated cuttings preparation system as shown schematically in FIG. 9, although the method can also be carried out manually. Regardless of whether the system is manual or automated, the same general sample preparation steps are preferably followed.

First, in step 101, a mineral sample is collected. For example, the mineral sample may be collected at a mine or at a well. For sampling a well, the mineral sample is typically collected from the drilling mud that is returning to the surface from bottom of the well. The mineral sample should be representative of the population being sampled.

In optional step 102, the mineral sample can be washed and/or dried, if necessary. Cuttings samples usually require drying before they can be processed through the remaining sample preparation stages. Cuttings samples may be moist due to drilling fluids, water, or hydrocarbon fluids. The level of moisture present will affect the drying time required for each sample. If a sample contains no observable moisture, for example, it may not need to go through the drying stage. Depending on the size of the original lot and the level of moisture, this step may be unnecessary or it may take considerable time in a drying oven at 45°-80° C. Preferably the sample is dried until the moisture in the sample is less than 0.5% by weight.

Figure 3:
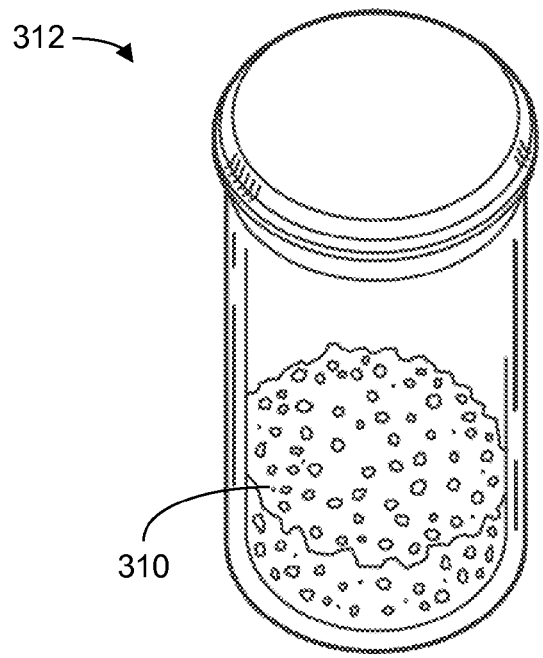
FIG. 3 shows a glass bottle for storing the aliquot before mixing with epoxy.

Once the sample has been dried, if necessary, it is preferably sub-sampled to create a smaller representative aliquot from the larger sample. For example, in optional step 104, the bulk dry sample may be screened through a suitably sized sieve, for example 2-3 mm, to remove coarse cuttings (which are sometimes not considered representative portions of the sample). In some applications, an original sample may be stage-crushed to maintain representivity and produce sufficiently small particles for embedding in the epoxy. In step 106, a rotary macro-splitter or coarse riffler can then be used to sub-divide the bulk sample into a number of smaller random sub-samples. It is preferable that at least one of the original smaller samples be stored so that it is available for further analysis if required. Finally, in step 108, a micro-riffler can be used to further sub-divide one of the sub-samples into an even smaller representative aliquot. Rifflers are commercially available, for example, from Quantachrome Instruments, Boynton Beach, Fla., USA. The final aliquot typically is of a predetermined amount, typically determined by volume or by weight, for example 4-5 grams of sample from an initial bulk sample of 1 kg. Determination by volume is preferred as that standardizes the sample packing density which is measured by volume. Referring also to FIG. 3, the final sample aliquot 310 can be stored in a plastic or glass vial 312 until ready to be mixed with fixing compound.

Once a representative sample of a suitable size has been separated, the aliquot is preferably mixed with an epoxy resin in a mold to produce a sample casting block. The objective of block casting is to mix the aliquot of sample with epoxy resin and cure the resin to create a sample block ready for sectioning. Block casting comprises three steps: combining the ingredients (typically the sample, epoxy, and hardener), mixing the ingredients, and curing the sample.

In preferred embodiments of the present invention using very rapid setting epoxy, combining the ingredients and mixing them is a very time critical step. With such rapid setting epoxy, it is desirable to commence mixing within 20-30 seconds after the epoxy, hardener, and sample mixture are combined. The rapid mixing is achieved using any suitable automatic mixing device, such as the devices commercially available from Thinky Corporation, Tokyo, Japan.

A suitable epoxy resin will preferably be a rapid curing, two-part epoxy, such as ARALDITE K219S, which is a two part epoxy available commercially from Huntsman Advanced Materials. A suitable epoxy resin for use with embodiments of the present invention will cure sufficiently for the particle positions to be fixed within 2-3 minutes and will have negligible amounts of shrinking even when fully cured.

In step 110, the desired amount of the fixing compound, such as epoxy and hardener (or part A and B), is added to the casting mold. For the K219S epoxy described above, the two parts of the epoxy should be mixed in equal quantities (ratio of 1:1), and with a sample of 4.5 g as described above, the total amount of epoxy and hardener added will preferably be approximately 7.5 g. The two-part epoxy is preferably added to the mold before the particulate sample to prevent a dry agglomeration of sample at the bottom of the mold. In some cases, it may be preferable to add the first part of the two-part epoxy, then the sample, and finally the epoxy hardener. For manual sample preparation, the steps of adding epoxy and sample can be performed on a scale to ensure accuracy.

Figure 2:
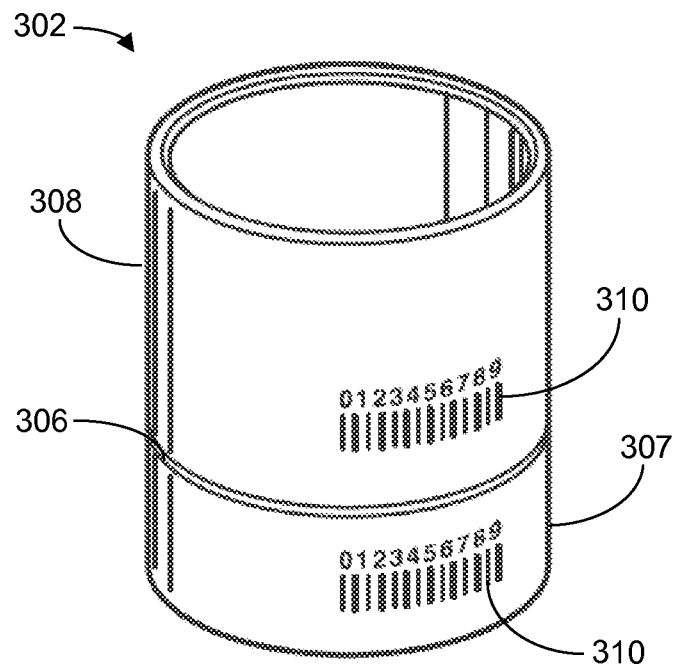
FIG. 2 shows a preferred integral mold used in the process of FIG. 1.

FIG. 2 shows an integral casting mold 302 which can be used in the process of FIG. 1. The mold is referred to as an integral mold because the sample is mixed directly in the mold, which then remains attached to the sample during the rest of the preparation process including slicing to expose a section face and measurement (although in some embodiments of the present invention prior art reusable molds could be used).

According to preferred embodiments of the present invention, an integral mold is preferably formed from a material that has a low surface energy so that it adheres to epoxy. This is directly contrary to the prior art, which teaches molds made of a material such as PTFE that can be more easily separated from the hardened epoxy. A suitable mold, for example, could be formed from a material such as ABS which adheres to epoxy, has a wall having an outside diameter of 30 mm, a wall thickness of 1 mm, a base thickness of 2 mm, and a height of 15 mm. The dimensions given are by way of example only and other suitable dimensions could be used.

In some preferred embodiments of the present invention, after the epoxy has hardened, the mold and the casting block are both placed into the slicing saw to be sectioned. In other words, the saw is used to slice through both the mold and the casting block, rather than removing the casting block from a re-usable plastic mold as in the prior art, to create a primary and a secondary sample section. Mold 302 also has a textured cut line 306 between the primary mold side 307 and the secondary mold side 308 (corresponding to the primary and secondary sample sections), which gives an indication of where the mold should be sliced. Using an integral mold not only saves time, but also eliminates a step (sample block removal from the mold) that is difficult to automate. Each mold is preferably uniquely identified, with the identification present on both the primary and secondary mold sections, and is designed to fit directly in the sample block holder.

Figure 10:
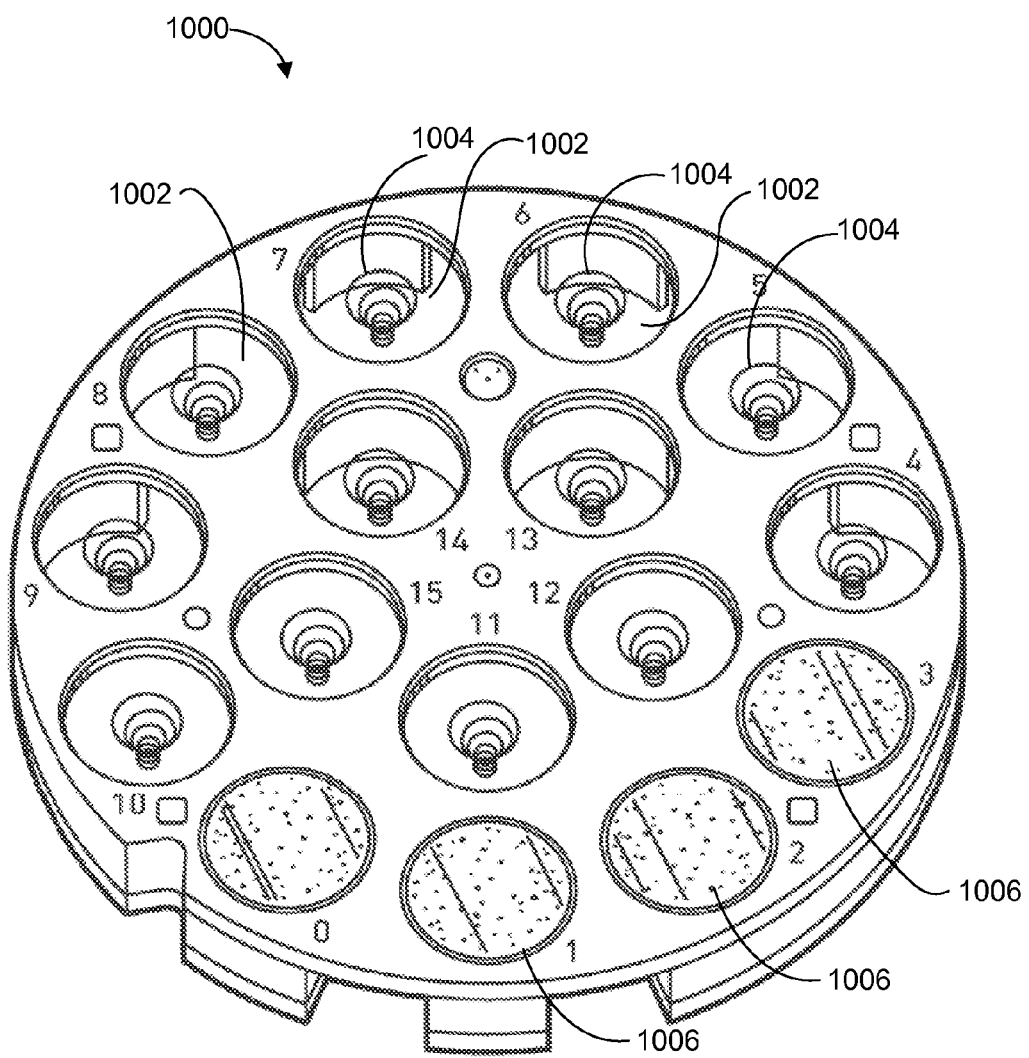
FIG. 10 shows a sample holder for holding multiple samples in an electron beam instrument or other analysis instrument.

The casting mold preferably includes a key or notch that serves to align the sample mold within a multi-sample sample carrier, such as the carrier shown in FIG. 10, and to enable automatic gripping of the mold in automatic systems. A preferred casting mold also includes one or more identifiers, such as a bar code or radio frequency identification circuit (RFID) 310 that provides easy tracking of the sample, preferably on both the primary and secondary sections. The identifier of the RFID can be matched to information that describes the date, time, and location where the sample was taken. Because the casting block preferably remains in the mold during slicing and even analysis, the identifier can be used to keep track of the desired information for a given sample throughout the sample preparation and measurement process.

Figure 4:
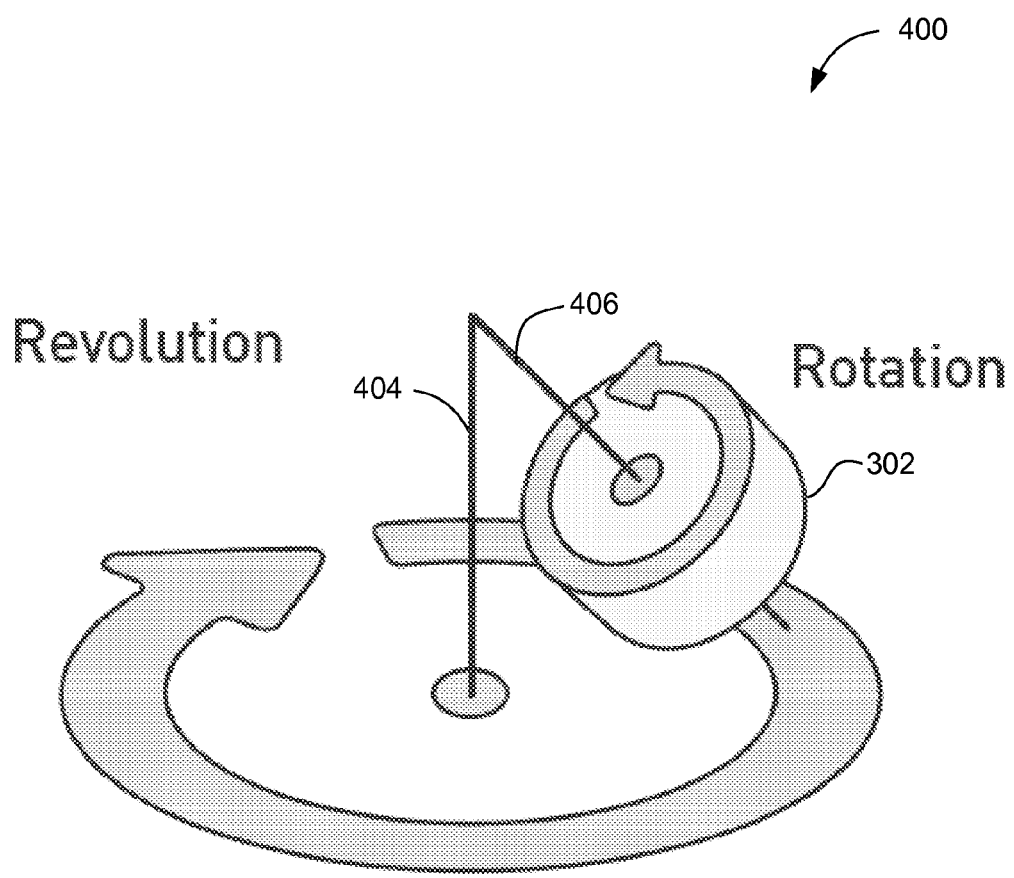
FIG. 4 shows schematically the planetary motion of a mixture used to automatically mix the sample and fixing compound during curing.

In step 112, the sample aliquot is added to the epoxy in the mold. In step 114, the sample, mold, and identifier is then placed in an automatic mixing machine. Once the two-part epoxy has been added to the mold, it is very desirable to add the particulate sample to the mold and to transfer the mold to the mixer to begin mixing as soon as possible, preferably in less than 30 seconds. The preferred mixing machine is capable of providing a uniform distribution of particles within the mold and preventing the coarser particles from settling to the bottom of the mold while the fixing compound is still soft. FIG. 4 shows schematically a preferred mixer 400. A preferred mixing machine provides a planetary motion, with the mold 302 rotating along a mold axis 406 and revolving around a mixer axis 404. The rotation speed about the mold axis 406 is preferably between about 500 rpm and about 1000 rpm, more preferably at about 800 rpm, while the mold revolves around the mixer axis 404, preferably between 1000 rpm and 3000 rpm, more preferably at about 2000 rpm. The mixer settings are optimized to maintain a consistency of the sample depending on the sample composition and the fixing compound. The mixer is preferably sufficiently fast to avoid settling of the particles while the fixing compound is curing, and also to remove trapped air from the fixing compound. Using the fast-setting epoxy as described above, the mixing time should be approximately 3 minutes.

In step 116, after the fixing compound is sufficiently cured to maintain the position of the particles in the molded sample, the mold can be removed from the mixer and cured further. Further curing may be done by leaving the sample to cure at room temperature, heating for a period of time, or, for example, by ultraviolet light curing. In some embodiments of the present invention, the molded sample can be further cured by heating in an oven at a temperature of about 45° C. for 5-10 minutes.

Figure 5:
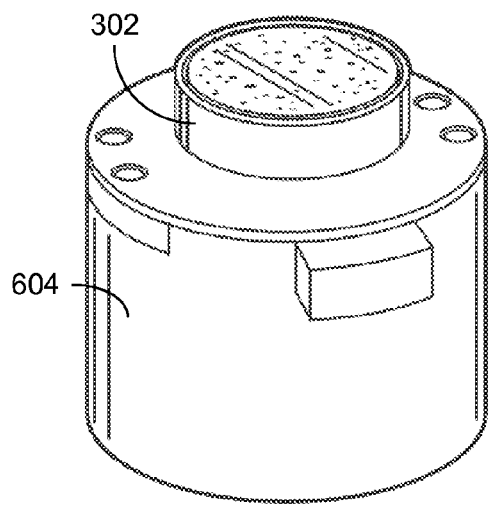
FIG. 5 shows the height setting jig assembly for a cut-off saw used to section the mold and cured sample according to preferred embodiments of the present invention.
Figure 6:
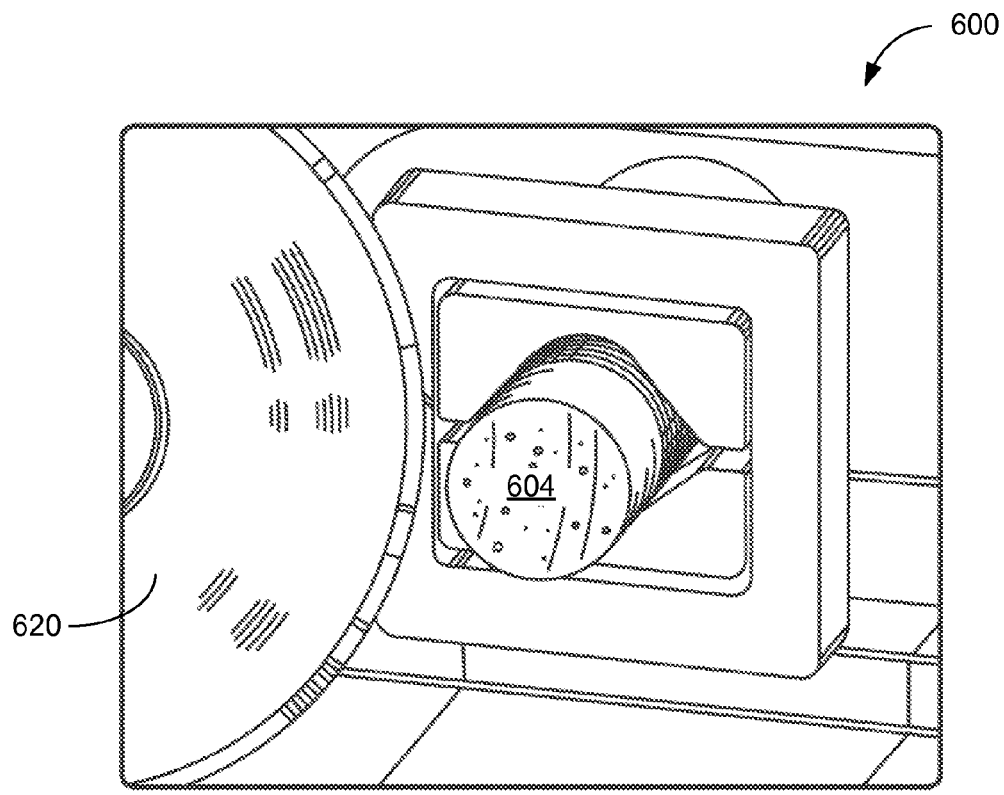
FIG. 6 shows the sample loaded into the sectioning saw after the top portion has been removed according to preferred embodiments of the present invention.

Referring to FIGS. 5 and 6, once the sample has been cured, the mold and sample (cast block 302) can be transferred to a cut-off saw 600 such as a Struers Accutom 50 for sectioning. The objective of sectioning is to create a random section through the block to expose the internal structure of the particles and provide a flat surface for x-ray analysis. The top portion of the sample block will usually not be representative, so it is desirable to cut a section off of the top of the block to expose a representative sample face. Preferably, the distance between the top of the molded sample block and the slice will be at least the diameter of the largest particles in the sample to achieve a truly representative sample. This helps ensure that the exposed section has a random distribution of particles, that is, that all particles have an equal probability of being measured. Typically, the sawed section height (the portion cut off the top of the sample) will be 2.5-4.5 mm. With grinding and polishing as in the prior art, it was difficult and very time consuming to grind back the required amount and it is rarely done correctly, thus introducing a significant bias into the sample. Sawing, in accordance with some embodiments of the invention, can replace grinding to create the section. Applicants have found unexpectedly that sawing produces a much better surface finish so that the grinding and polishing becomes unnecessary in some applications.

The cast block is then fitted to the saw chuck 604 so that a standard distance is exposed by the chuck without the need for further measurement. This is preferably done with a height setting gauge, preferably part of the chuck 604. To cut a block accurately, the block must be held tightly in the saw chuck and positioned to cut off a standard length. The use of a height setting gauge properly aligns the casting block so that when multiple samples are processed the saw slices each mold and sample at about the same point. Thus, the need for manual adjustment of the position of the casting block 302 in the chuck is eliminated, which facilitates automation.

In step 118, the mold and the cured sample block are sliced to expose the internal structure of the particles and provide a flat surface 604 for x-ray analysis. A preferred saw blade 620 is a diamond saw such as a Struers EOD15. A cooling fluid, such as water or kerosene is preferably used to minimize heat during sample sectioning. The blade 620 should produce a smooth surface. A preferred cut-off saw can be adjusted to provide a saw speed of 300 to 5,000 rpm, a sawing stroke of 25-45 mm, and a sawing rate of 100-600 µm/sec. Preferably, the blade positioning accuracy will be at least 5 µm. In a preferred embodiment of the present invention, the mold and cured sample will be sectioned using a diamond saw blade having a blade speed of 5000 rpm, a sawing stroke of 35 mm, and a cutting rate of 300 µm/sec. This would result in a typical sectioning time of approximately 3 minutes.

Figure 7A:
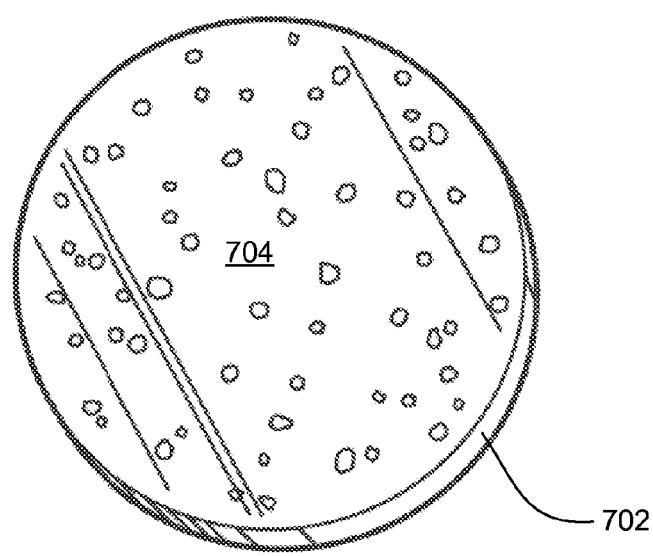
FIGS. 7A and 7B show sample blocks prepared according to preferred embodiments of the present invention.
Figure 7B:
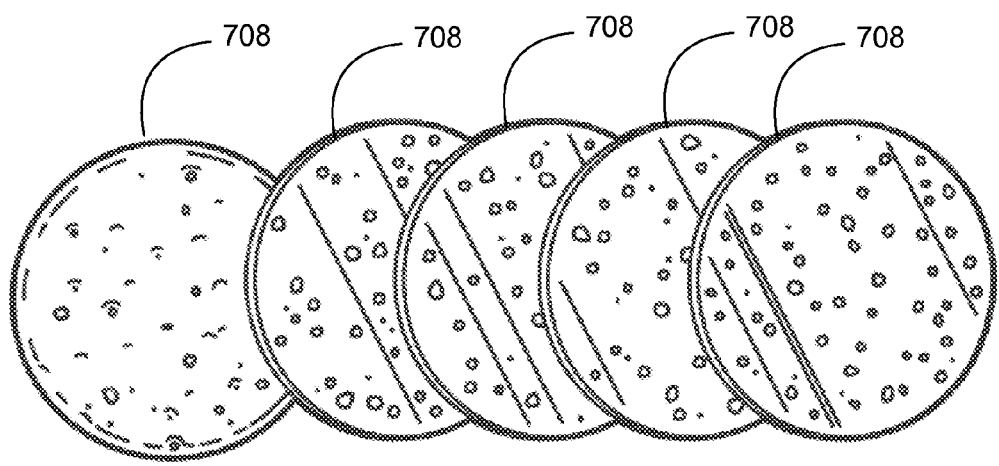

Once the sectioning is complete, both the cut-off section and the sample block can be retained as a primary and secondary sample. Both samples (also called "pucks") preferably have a smooth exposed sample face. FIG. 7A shows an example of a puck 702 having a smooth exposed sample face 704. Multiple slices may be made by further sawing at an appropriate distance apart to increase the number of particles exposed for measurement from a single mold. FIG. 7B shows a series of slices 708, which can be as thin as 2 mm and still be suitable for measurement. The sample block is preferably short enough to fit into existing sample carriers, such as the one shown in FIG. 10, that is, less than about 15 mm. The sample block should be thick enough to be able to cut multiple sections in series. In one embodiment, the sample block is about 10 mm. Preferably each section will have a uniform distribution of particles on the sample face. Using the sectioning techniques described above, the surface flatness across the entire cut surface is preferably no more than 100 µm, while the surface roughness (quantified by the largest difference from peak-to-valley for variations in height on the surface) would be no more than 50 µm, more preferably no more than 25 µm and most preferably less than 10 µm.

Applicants have discovered that, contrary to prior art practice, the sample surface after slicing is sufficiently smooth in many cases for viewing, making the grinding and polishing steps unnecessary. Some samples may benefit from being polished after slicing, but can be analyzed without grinding. Yet other samples may still require grinding or polishing. After the sample is sliced, it is optionally ground and/or polished in step 120. Whether or not a sample requires polishing depends on the properties of the sample, such as the particle size and composition. Preferably, most or all of the grinding and polishing steps of the prior art are eliminated according to preferred embodiments of the present invention. Eliminating some or all of the grinding and/or polishing steps not only saves time, it also facilitates automation of the sample preparation process as described above.

After sectioning, in step 122 the sample block is preferably air dried at 45° C. for 1-2 minutes to remove any water remaining from the sawing process. The image of the cut surface of the sample is then recorded by a high resolution color camera, preferably at a resolution of about 4 Megapixels.

After the sample is sliced and optionally ground and/or polished, in step 124 the sample block is placed in carbon coater, the carbon coater is evacuated to the specified vacuum, and the carbon arc is used to coat the sample to the required thickness. A conductive coating, such as for example a carbon coating, is used to make the surface of the sample block conductive to avoid a build-up of negatively charged electrons, which can result in discharges that lead to irregularities in the Backscattered Electron (BSE) signal and alter the landing energy of the electron beam thus distorting the x-ray spectrum. Because the thickness of the carbon coat has an impact on the BSE signal intensity, it is desirable that samples are coated under standard conditions to the same thickness. In a preferred embodiment, a carbon coating of 15-45 nm can be applied using a carbon coater apparatus via carbon evaporation using graphite rods. If the analysis is to be performed in a charged particle system that includes a charge neutralization means, such as an electron flood gun, the conductive coating may be unnecessary.

Before and after the conductive coating is applied, an image of the sample surface is formed by a camera, and the image is reviewed, either by a person or by image recognition software, to confirm that the sample is properly prepared and that the surface is properly prepared for illuminating with an electron beam for analysis. The sample is transferred in step 126 to an electron beam instrument or other analytical instrument for analysis. If it is determined in decision step 128 that other samples are to be prepared, the process repeats from step 102.

Figure 8:
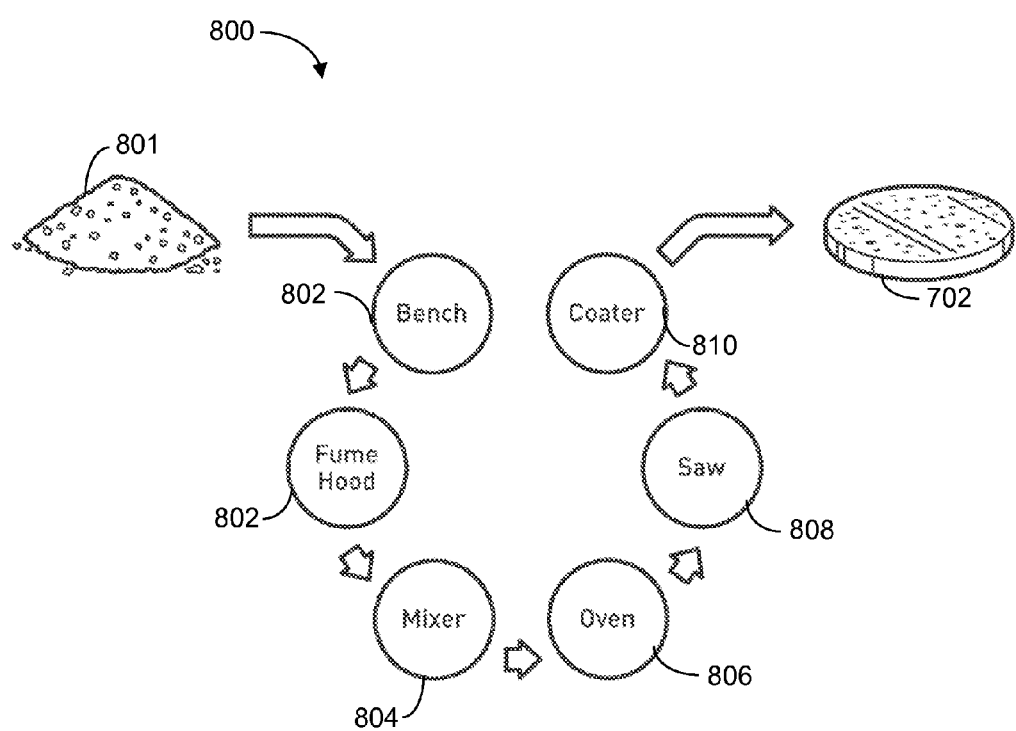
FIG. 8 shows a possible ergonomic arrangement of sample preparation stations to facilitate manual or robotic sample preparation according to preferred embodiments of the present invention.
Figure 9:
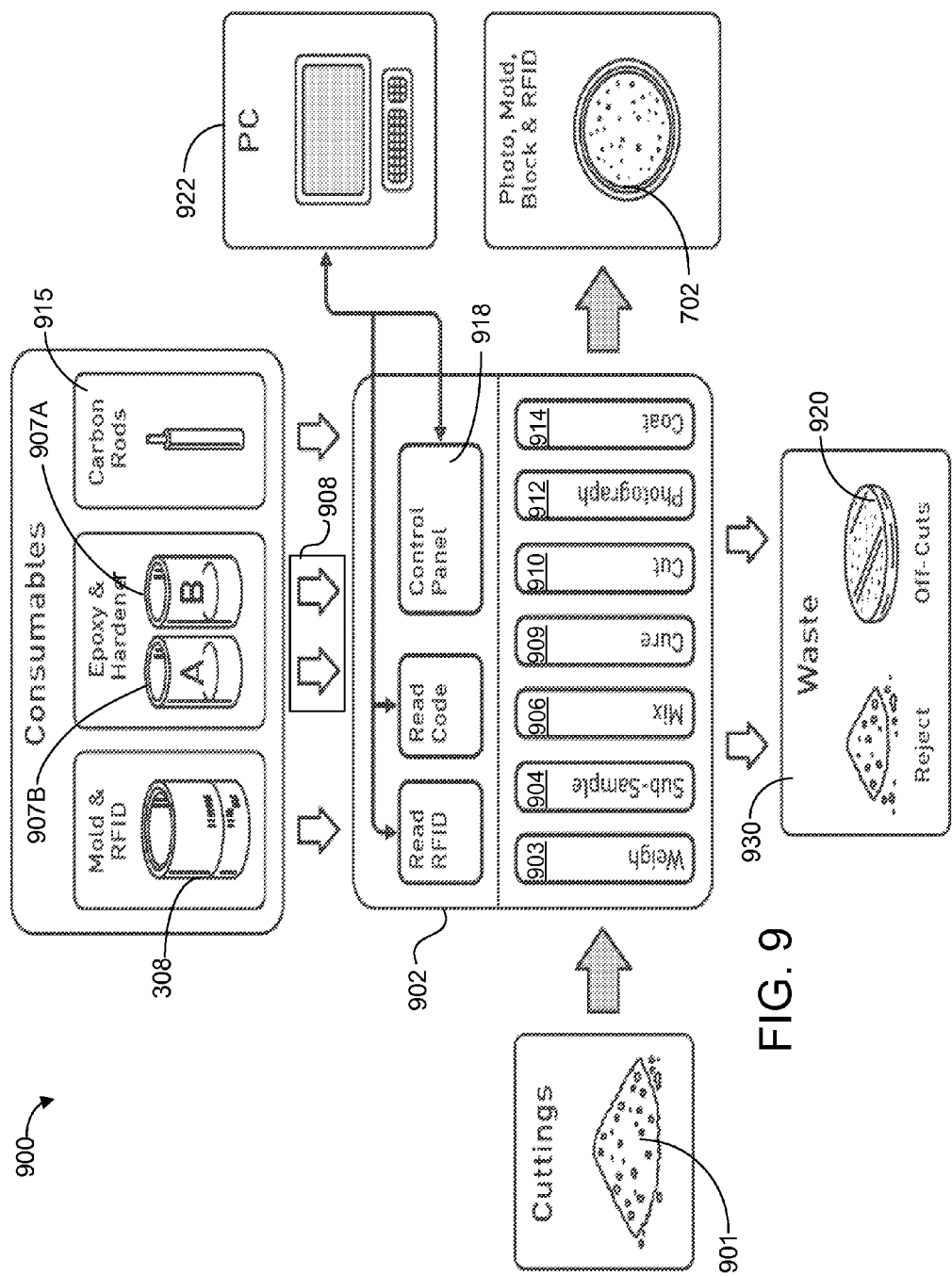
FIG. 9 shows an automated cuttings preparation system according to preferred embodiments of the present invention.

As discussed above, the preparation steps of FIG. 1 can be carried out manually by one or more operators. For manual or robotic preparation, it is desirable to arrange the equipment and sample prep stations in an ergonomic manner to facilitate the transfer of the sample from stage to stage of the preparation process, as shown in FIG. 8. The sample bench 802 could be used for the initial preparation of the sample 801 and for the sub-sampling operations. Fume hood 803 could also hold a scale so that the precise amounts of rapid setting epoxy (parts A and B) and the sample aliquot can be added to the mold and to remove epoxy fumes. The filled mold is then transferred to the Mixer 804, where the sample is mixed for approximately 3 minutes. The partially cured sample can then be left on the bench or transferred to the oven 806 for final curing. The cured sample and mold would then be transferred to saw 808 and sectioned. And finally, the sectioned sample block would be transferred to the carbon coater 810, which produces final sample 702. Careful arrangement of the various stations as in FIG. 8 is highly desirable given the desire for a fast preparation time and the rapid setting of the epoxy used in preferred embodiments of the present invention. Persons of skill in the art will recognize that there are a number of steps that can be taken to further optimize the transfer time, such as preparing a new mold during the mixing, curing and coating time of the previous mold, More preferably, the method of FIG. 1 is carried out by way of an automated cuttings preparation system as shown in FIG. 9. An automated cuttings preparation system according to preferred embodiments of the present invention is an automated self-contained unit for the complete end-to-end processes of manufacturing a single sample ready for presentation to automated mineralogy systems. In particular, the system can preferably be used to prepare drill cuttings for presentation to a well-site measurement electron beam system used in remote locations or on oil rigs and mine sites. In a preferred embodiment of an automated cuttings preparation system, a user will be able to pour a dry sample into a stainless steel cup and place it on an input tray. After about 15 minutes, a fully prepared sample will emerge, ready for insertion into the electron beam tool for analysis. The end-to-end process can be referred to informally as "Powder to Puck" (P2P). Preferred embodiments of a P2P system will dry and weigh the cuttings, sub-sample the cuttings to create a random aliquot, mix the aliquot thoroughly with an epoxy resin to create a cast block, heat the epoxy to cure it, cut a random section through the block, photograph the surface of the block, and finally coat the sample with a conductive coating.

The automated cuttings preparation system 900 of FIG. 9 includes all of the systems described above in the method of FIG. 1, including a weighing system 903, a sub-sampling system 904, a mixing system 906, a curing system 909 (such as an oven or UV light) for curing samples, a cutting system (such as a sectioning saw), an imaging system 912, and a conductive coating system 914. Additionally, an automated dispensing system 908 can be used to dispense predetermined amounts of both parts of the two-part epoxy resin 907A and 907B. As shown in FIG. 9, some or all of the systems described herein, such as the dispensing, sample adding, mixing, and curing systems, can be combined into a single machine. For example, the fixing compound can be dispensed in the mold with the sample while the mold is loaded in the mixing machine. The sample could also be heated while in the mixing machine, during mixing or after mixing, to cure the sample. The optimum combination will depend on the application including factors such as desired throughput, that is, the number of samples to be processed per hour. Alternatively, pick and place robots (not shown) can be used to move the mold from separate machine to separate machine, such as an epoxy dispensing machine, a sample adding machine, a mixing machine, and an oven (for further sample curing).

As shown schematically in FIG. 9, in a preferred embodiment, a sample 901 can be loaded into the system input 902 by placing approximately 1 kg of dry particulate sample into a stainless steel cup. In the embodiment of FIG. 9, it is assumed that the sample has already been washed and dried, although stations to wash and dry the sample could also be incorporated into the automated system. Preferably, the cup is labeled with sample identifying information, for example with a bar code. The sample can be logged into the system manually by an operator or by way of an integrated bar code reader that can input the bar code to record matching sample information into the system database.

A scale in weighing system 903 allows the system to automatically weigh an incoming sample and to automatically set the sub-sampling unit 904 to create the representative aliquot of the desired size (for example, 4.5 g). Sub-sampling unit 904 automatically creates a representative aliquot by volume ready for adding to the mold using the method described above. Left over cuttings can be saved in the original steel cup (with bar code) and transferred to a waste storage area 930.

A mold hopper is used to transfer new tagged molds 308 from sub-sampling unit 904 to the mixer 906. Once a new mold has been loaded, the identifying tag on the mold is read and the ID linked to the sample information in the database. The bar code on the mold is read by a bar code reader (not shown) and the ID linked to both the primary and secondary sample information in the database.

An automated dispensing system can be used to dispense a specified dose of epoxy and hardener and then the aliquot of sample is added. The epoxy and sample aliquot will then be mixed in the mold by the planetary mixer for the specified time and with the specified speed settings. After mixing, the integral mold, sample, and RFID (the casting mold) can be transferred to a curing oven 909 at the specified temperature for the specified time. Alternatively, the mixer itself could be contained within such an oven.

The cast block is then transferred from the curing oven to the cut-off saw 910. The entire casting block (mold and cured sample block) are sliced at the desired height by using a suitably sized height setting jig. The cut-off portion of the casting block can be discarded, while the remaining sample block is dried for a specified time at a specified temperature. In preferred embodiments, no grinding or polishing of the sample block face will be required.

An image of the cut surface of the sample can be recorded by a high resolution color camera 912. And the sample can then be moved to the carbon coater 914, which is evacuated to the specified vacuum and a carbon arc is used to coat the sample with a layer of carbon to the required thickness. The final sample 702 can then be ejected from the system onto the Output Tray with the cut surface facing upwards as shown. According to preferred embodiments of the present invention, a fully prepared sample will emerge, ready for insertion into the electron beam tool for analysis, in as little as 15-25 minutes. After the sample is prepared, it can be loaded into an electron beam system for analysis, either singly or in a batch of samples, for example, in a sample tray such as the one shown in FIG. 10.

FIG. 10 shows a sample holder 1000 including multiple numbered openings 1002 having diameters slightly smaller than a sample 1006. Each opening 1002 has a spring 1004 to press a sample 1006 against the opening 1004 to align the top of sample 1006 relative to the top of sample holder 1000.

Figure 11:
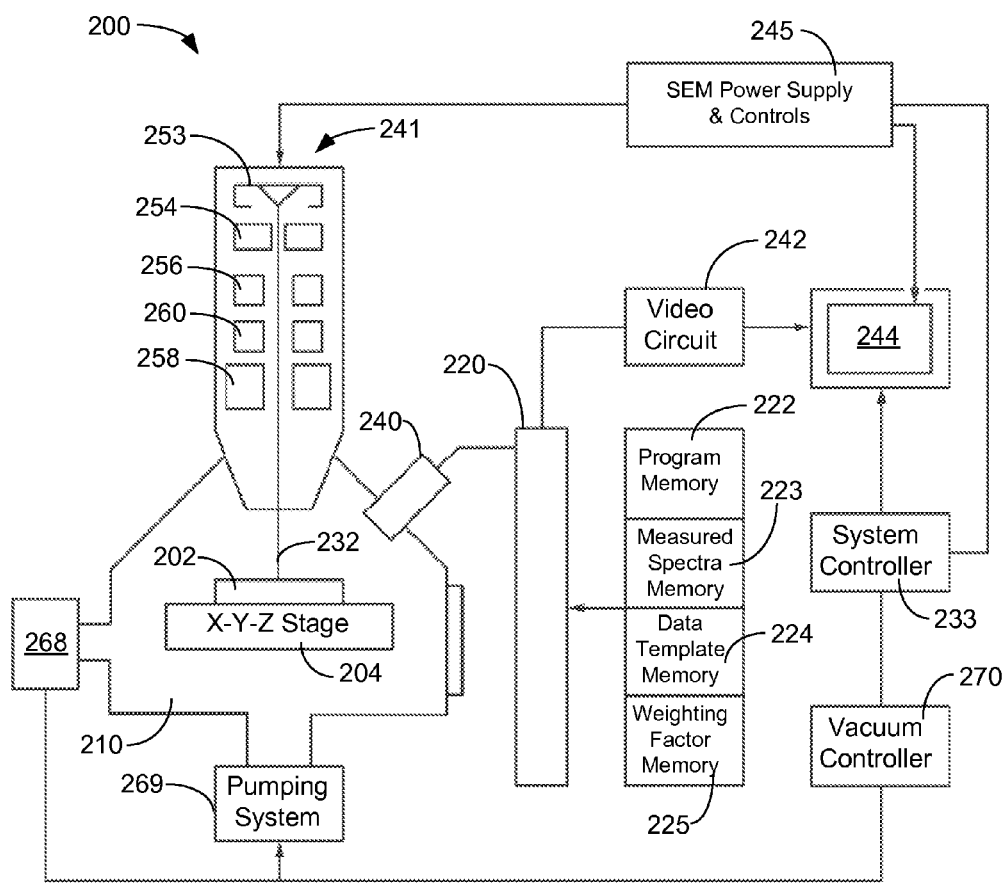
FIG. 11 shows a scanning electron beam system with an x-ray detector suitable for analyzing samples prepared according to preferred embodiments of the present invention.

FIG. 11 shows a scanning electron beam system 200 with an x-ray detector 240 suitable for analyzing samples prepared according to the present invention. A scanning electron microscope 241, along with power supply and control unit 245, is provided with system 200. An electron beam 232 is emitted from a cathode 253 by applying voltage between cathode 253 and an anode 254. Electron beam 232 is focused to a fine spot by means of a condensing lens 256 and an objective lens 258. Electron beam 232 is scanned two-dimensionally on the specimen by means of a deflection coil 260. Operation of condensing lens 256, objective lens 258, and deflection coil 260 is controlled by power supply and control unit 245.

A system controller 233 controls the operations of the various parts of scanning electron beam system 200. The vacuum chamber 210 is evacuated with ion pump 268 and mechanical pumping system 269 under the control of vacuum controller 270.

Electron beam 232 can be focused onto sample 202, which is on movable X-Y stage 204 within lower vacuum chamber 210. When the electrons in the electron beam strike sample 202, the sample gives off x-rays whose energy correlates to the elements in the sample. X-rays having energy inherent to the elemental composition of the sample are produced in the vicinity of the electron beam incident region. Emitted x-rays are collected by x-ray detector 240, preferably an energy dispersive detector of the silicon drift detector type, although other types of detectors could be employed, which generates a signal having an amplitude proportional to the energy of the detected x-ray.

Output from detector 240 is amplified and sorted by the processor 220, which counts and sorts the total number of x-rays detected during a specified period of time, or a fixed total count at a selected energy and energy resolution, and a channel width (energy range) of preferably between 10-20 eV per channel. Processor 220 can comprise a computer processor; operator interface means (such as a keyboard or computer mouse); program memory 222 for storing data and executable instructions; interface means for data input and output, executable software instructions embodied in executable computer program code; and display 244 for displaying the results of a multivariate spectral analysis by way of video circuit 242.

Processor 220 can be a part of a standard laboratory personal computer, and is typically coupled to at least some form of computer-readable media. Computer-readable media, which include both volatile and nonvolatile media, removable and non-removable media, may be any available medium that can be accessed by processor 220. By way of example and not limitation, computer-readable media comprise computer storage media and communication media. Computer storage media include volatile and nonvolatile, removable and non-removable media implemented in any method or technology for storage of information such as computer-readable instructions, data structures, program modules or other data. For example, computer storage media include RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium that can be used to store the desired information and that can be accessed by processor 220.

Program memory 222 can include computer storage media in the form of removable and/or non-removable, volatile and/or nonvolatile memory and can provide storage of computer-readable instructions, data structures, program modules and other data. Generally, the processor 220 is programmed by means of instructions stored at different times in the various computer-readable storage media of the computer. Programs and operating systems are typically distributed, for example, on floppy disks or CD-ROMs. From there, they are installed or loaded into the secondary memory of a computer. At execution, they are loaded at least partially into the computer's primary electronic memory. The invention described herein includes these and other various types of computer-readable storage media when such media contain instructions or programs for implementing the steps described below in conjunction with a microprocessor or other data processor. The invention also includes the computer itself when programmed according to the methods and techniques described herein.

An x-ray spectrum obtained as described above can be stored in a portion of memory 222, such as the measured spectra memory portion 223. Data template memory portion 224 stores data templates, such as known spectra of elements or, in some embodiments, known diffraction patterns of materials. Weighting Factor Memory portion 225 stores weighting factor for each of the data templates, the weighting factors combining with the data templates to produce a calculated spectrum approximating the measured spectrum. The weighting factors correlated to the abundance in the sample of the element corresponding to the data template. Processor 220 uses the methods described above to minimize an error value which represents the difference between the measured pattern and the combination of the data templates and weighting factors.

While the embodiment shown includes a scanning electron microscope, related embodiment could use a transmission electron microscope or a scanning transmission electron microscope to generate x-rays from the sample. An x-ray fluorescence system could also be used to generate x-rays from the sample. Other embodiments may detect other characteristic radiation, such as gamma rays, from a sample.

In accordance with some embodiments of the invention, a method of preparing samples for analysis in an electron beam system, the method comprising: collecting a mineral sample for analysis, drying the sample, dividing the collected sample into a smaller representative aliquot, adding together the aliquot and the two components of a rapid-setting two-part fixing agent in a sample mold, the fixing agent rubberizing within 3 min, adding the aliquot to the fixing agent in the mold, mixing the aliquot and fixing agent in the mold in an automating mixer, said mixing beginning within 30 seconds of adding the aliquot to the fixing agent in the mold, allowing the fixing agent to cure to form a cured sample block within the mold, sectioning the mold and the cured sample block to remove the top portion of the cured sample block and expose a flat interior sample face, and without grinding or polishing the sample face, coating the sample face with a layer of a conductive material to produce a sample for analysis.

In accordance with some embodiments of the invention, a method of preparing samples for analysis in an electron beam system, the method comprising: combining the sample with an uncured fixing agent, mixing the sample and the fixing agent in a mold in an automatic mixer, allowing the fixing agent to cure to form a cured sample block within the mold, sectioning the mold and the cured sample block to remove the top portion of the cured sample block and expose a flat interior sample face, and coating the sample face with a layer of a conductive material to produce a sample for analysis.

In some embodiments, the cured sample block is not ground before coating the sample face with the layer of conductive material. In some embodiments, the cured sample block is not polished before coating the sample face with the layer of conductive material.

In some embodiments, sectioning the mold and the cured sample block includes slicing the mold and the cured sample block using a saw. And in some embodiments, slicing the mold and the cured sample using a saw includes using a non-water based cutting fluid.

In some embodiments, combining the sample with an uncured fixing agent includes combining the sample with the fixing agent in the mold. In some embodiments, combining the sample with an uncured fixing agent includes combining the aliquot with a fixing agent that fixes the position of the sample particles within the mold in less than five minutes. In some embodiments, mixing the sample and the fixing agent in a mold in an automating mixer includes beginning to mix the aliquot and the fixing agent in the mixer within 30 seconds of adding the aliquot to the fixing agent.

In some embodiments, the method of preparing samples for analysis further comprises: collecting a mineral sample for analysis, drying the mineral sample, and dividing the collected mineral sample into a smaller representative sample.

In some embodiments, collecting a mineral sample for analysis includes collecting a sample from drilling mud returned from a well. And in some embodiments, collecting a mineral sample for analysis includes collecting a sample from a mine.

In some embodiments, combining the sample with an uncured fixing agent, mixing the sample and the fixing agent in a mold in an automatic mixer, allowing the fixing agent to cure to form a cured sample block within the mold, and sectioning the mold and the cured sample block to remove the top portion of the cured sample block and expose a flat interior sample face, are preformed automatically.

In accordance with some embodiments of the invention, an apparatus for preparing a mineral sample, comprises: a dispensing system for dispensing an uncured fixing agent, a mixing system for mixing the uncured fixing agent with the mineral sample in a mold, a sectioning saw for slicing the cured fixing agent and the mineral sample in the mold, the sectioning saw providing a surface on the sample sufficiently smooth for electron beam sample analysis.

In some embodiments, the sectioning saw provides a surface flatness across the entire cut surface better than 100 µm. In some embodiments, the surface roughness defined as the largest difference from peak-to-valley for variations in height on the surface is no more than 25 µm.

In some embodiments, the apparatus for preparing a mineral sample further comprises an imaging system for observing the sample after it is sliced. In some embodiments, the apparatus for preparing a mineral sample further comprises a conductive coater for coating the surface of the sample after it is sliced. In some embodiments, the apparatus for preparing a mineral sample further comprises a weighing system for dispensing a specified amount of mineral. In some embodiments, the apparatus for preparing a mineral sample further comprises a sub-sampling system for procuring a representative mineral sample from a larger mineral sample.

A preferred method or apparatus of the present invention has many novel aspects, and because the invention can be embodied in different methods or apparatuses for different purposes, not every aspect need be present in every embodiment. Moreover, many of the aspects of the described embodiments may be separately patentable. The invention has broad applicability and can provide many benefits as described and shown in the examples above. The embodiments will vary greatly depending upon the specific application, and not every embodiment will provide all of the benefits and meet all of the objectives that are achievable by the invention.

It should be recognized that embodiments of the present invention can be implemented via computer hardware, a combination of both hardware and software, or by computer instructions stored in a non-transitory computer-readable memory. The methods can be implemented in computer programs using standard programming techniques—including a non-transitory computer-readable storage medium configured with a computer program, where the storage medium so configured causes a computer to operate in a specific and predefined manner—according to the methods and figures described in this Specification. Each program may be implemented in a high level procedural or object oriented programming language to communicate with a computer system. However, the programs can be implemented in assembly or machine language, if desired. In any case, the language can be a compiled or interpreted language. Moreover, the program can run on dedicated integrated circuits programmed for that purpose.

Further, methodologies may be implemented in any type of computing platform, including but not limited to, personal computers, mini-computers, main-frames, workstations, networked or distributed computing environments, computer platforms separate, integral to, or in communication with charged particle tools or other imaging devices, and the like. Aspects of the present invention may be implemented in machine readable code stored on a non-transitory storage medium or device, whether removable or integral to the computing platform, such as a hard disc, optical read and/or write storage mediums, RAM, ROM, and the like, so that it is readable by a programmable computer, for configuring and operating the computer when the storage media or device is read by the computer to perform the procedures described herein. Moreover, machine-readable code, or portions thereof, may be transmitted over a wired or wireless network. The invention described herein includes these and other various types of non-transitory computer-readable storage media when such media contain instructions or programs for implementing the steps described above in conjunction with a microprocessor or other data processor. The invention also includes the computer itself when programmed according to the methods and techniques described herein.

Computer programs can be applied to input data to perform the functions described herein and thereby transform the input data to generate output data. The output information is applied to one or more output devices such as a display monitor. In preferred embodiments of the present invention, the transformed data represents physical and tangible objects, including producing a particular visual depiction of the physical and tangible objects on a display.

While the examples provided above describe the use of the present invention to prepare samples for EDS analysis, the invention can also be used to prepare samples for other types of analysis, including optical microscopy, WDS, XRD, or XFR.

Although much of the previous description is directed at mineral samples from drill cuttings, the invention could be used to prepare samples of any suitable material. The terms "work piece," "sample," "substrate," and "specimen" are used interchangeably in this application unless otherwise indicated. Further, whenever the terms "automatic," "automated," or similar terms are used herein, those terms will be understood to include manual initiation of the automatic or automated process or step.

In the following discussion and in the claims, the terms "including" and "comprising" are used in an open-ended fashion, and thus should be interpreted to mean "including, but not limited to . . . ." To the extent that any term is not specially defined in this specification, the intent is that the term is to be given its plain and ordinary meaning. The accompanying drawings are intended to aid in understanding the present invention and, unless otherwise indicated, are not drawn to scale. Particle beam systems suitable for carrying out the present invention are commercially available, for example, from FEI Company, the assignee of the present application.

Although the present invention and its advantages have been described in detail, it should be understood that various changes, substitutions and alterations can be made to the embodiments described herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

I claim as follows:

1. A method of preparing samples for analysis in an electron beam system, the method comprising:
    collecting a mineral sample for analysis;
    drying the sample;
    dividing the collected sample into a smaller representative aliquot;
    adding together the aliquot and the two components of a rapid-setting two-part fixing agent in a sample mold, the fixing agent rubberizing within 3 min;
    mixing the aliquot and fixing agent in the mold in an automating mixer, said mixing beginning within 30 seconds of adding the aliquot to the fixing agent in the mold;
    allowing the fixing agent to cure to form a cured sample block within the mold; sectioning the mold and the cured sample block to remove the top portion of the cured sample block and expose a flat interior sample face; and
    without grinding or polishing the sample face, coating the sample face with a layer of a conductive material to produce a sample for analysis.

2. A method of preparing samples for analysis in an electron beam system, the method comprising:
    combining the sample with an uncured fixing agent;
    mixing the sample and the fixing agent in a mold in an automatic mixer;
    allowing the fixing agent to cure to form a cured sample block within the mold;
    sectioning the mold and the cured sample block to remove the top portion of the cured sample block and expose a flat interior sample face; and coating the sample face with a layer of a conductive material to produce a sample for analysis.

3. The method of claim 2 in which the cured sample block is not ground before coating the sample face with the layer of conductive material.

4. The method of claim 2 in which the cured sample block is not polished before coating the sample face with the layer of conductive material.

5. The method of claim 2 in which sectioning the mold and the cured sample block includes slicing the mold and the cured sample block using a saw.

6. The method of claim 5 in which slicing the mold and the cured sample using a saw includes using a non-water based cutting fluid.

7. The method of claim 2 in which combining the sample with an uncured fixing agent includes combining the sample with the fixing agent in the mold.

8. The method of claim 2 in which combining the sample with an uncured fixing agent includes combining the aliquot with a fixing agent that fixes the position of the sample particles within the mold in less than five minutes, while producing a bubble-free cured sample block with no density segregation of the aliquot.

9. The method of claim 2 in which mixing the sample and the fixing agent in a mold in an automating mixer includes beginning to mix the aliquot and the fixing agent in the mixer within 30 seconds of adding the aliquot to the fixing agent while producing a bubble-free cured sample block with no density segregation of the aliquot.

10. The method of claim 2 further comprising:
collecting a mineral sample for analysis;
drying the mineral sample; and
dividing the collected mineral sample into a smaller representative sample.

11. The method of claim 10 in which collecting a mineral sample for analysis includes collecting a sample from drilling mud returned from a well.

12. The method of claim 10 in which collecting a mineral sample for analysis includes collecting a sample from a mine.

13. The method of claim 2 in which:
combining the sample with an uncured fixing agent;
mixing the sample and the fixing agent in a mold in an automatic mixer;
allowing the fixing agent to cure to form a cured sample block within the mold; and
sectioning the mold and the cured sample block to remove the top portion of the cured sample block and expose a flat interior sample face,
are preformed automatically.

* * * * *